United States Patent [19]

Clements-Jewery et al.

[11] 4,350,697
[45] Sep. 21, 1982

[54] ANTIDEPRESSANT AND NEUROLEPTIC BENZOTHIOPYRANO [2,3-C]-PYRIDINES

[75] Inventors: Stephen Clements-Jewery, Near Swindon; Robert Westwood, Faringdon; Peter W. Hairsine, Swindon, all of England

[73] Assignee: Roussel Uclaf, Paris, France

[21] Appl. No.: 240,392

[22] Filed: Mar. 4, 1981

[30] Foreign Application Priority Data

Mar. 6, 1980 [GB] United Kingdom ............... 8007660

[51] Int. Cl.³ .................. A61K 31/445; C07D 495/04
[52] U.S. Cl. ...................................... 424/256; 546/80
[58] Field of Search .......................... 546/80; 424/256

[56] References Cited

U.S. PATENT DOCUMENTS 3,275,640  9/1966  Engelhardt et al. ............... 546/202
3,583,997  6/1971  Ebnother et al. ..................... 546/80

Primary Examiner—Richard A. Schwartz
Attorney, Agent, or Firm—Hammon & Littell, Weissenberger and Muserlian

[57] ABSTRACT

Novel compounds selected from the group consisting of compounds of the formula

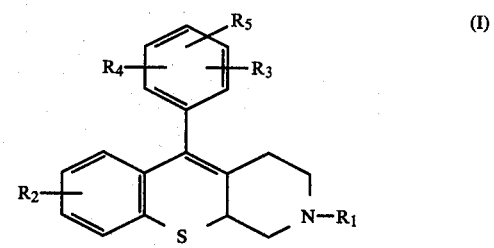

wherein $R_1$ is selected from the group consisting of hydrogen and alkyl of 1 or 5 carbon atoms, $R_2$ is selected from the group consisting of hydrogen, halogen and methyl, $R_3$, $R_4$ and $R_5$ are individually selected from the group consisting of hydrogen, halogen, alkyl of 1 to 5 carbon atoms, alkoxy of 1 to 3 carbon atoms, $-NH_2$ and mono- and dialkylamino of 1 to 3 alkyl carbon atoms and their non-toxic, pharmaceutically acceptable acid addition salts having antidepressant and neuroleptic activity and their preparation.

21 Claims, No Drawings

ANTIDEPRESSANT AND NEUROLEPTIC BENZOTHIOPYRANO [2,3-C]-PYRIDINES

OBJECTS OF THE INVENTION

It is an object of the invention to provide the novel compounds of formula I and their non-toxic, pharmaceutically acceptable acid addition salts and a novel process for their preparation.

It is another object of the invention to provide novel antidepressant and neuroleptic compositions and to provide a novel method of inducing antidepressant and neuroleptic activity in warm-blooded animals.

These and other objects and advantages of the invention will become obvious from the following detailed description.

THE INVENTION

The novel compounds of the invention are selected from the group consisting of compounds of the formula

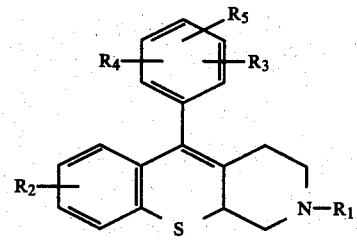

wherein $R_1$ is selected from the group consisting of hydrogen and alkyl of 1 to 5 carbon atoms, $R_2$ is selected from the group consisting of hydrogen, halogen and methyl, $R_3$, $R_4$ and $R_5$ are individually selected from the group consisting of hydrogen, halogen, alkyl of 1 to 5 carbon atoms, alkoxy of 1 to 3 carbon atoms, —$NH_2$ and mono- and dialkylamino of 1 to 3 alkyl carbon atoms and their non-toxic, pharmaceutically acceptable acid addition salts.

Examples of suitable halogens are chlorine, bromine and iodine. Examples of alkyl of 1 to 5 carbon atoms are methyl, ethyl, propyl, isopropyl, butyl, tert.-butyl, sec.-butyl and pentyl. Examples of alkoxy of 1 to 3 carbon atoms are methoxy, ethoxy, propoxy and isopropoxy and examples of mono and dialkylamino are methylamino, ethylamino, dimethylamino and diethylamino.

Examples of acids for the preparation of the non-toxic, pharmaceutically acceptable acid addition salts are inorganic acids such as hydrochloric acid, hydrobromic acid, hydriodic acid, nitric acid, sulfuric acid and phosphoric acid and organic acids such as propionic acid, acetic acid, formic acid, benzoic acid, maleic acid, fumaric acid, succinic acid, tartaric acid, citric acid, oxalic acid, glyoxylic acid and aspartic acid, alkanesulfonic acids such as methanesulfonic acid; and arylsulfonic acids such as benzenesulfonic acid.

Preferred compounds of formula I are those wherein $R_1$ is methyl and those wherein $R_2$ is hydrogen. Particularly preferred compounds of the invention are: 2-methyl-5-phenyl-1,3,4,10a-tetrahydro-2H[1]benzothiopyrano [2,3-c]pyridine, 2-methyl-5-(4-tolyl)-1,3,4,10a-tetrahydro-2H[1]benzothiopyrano[2,3-c]pyridine, 2-methyl-5-(2,4-dimethylphenyl)-1,3,4,10a-tetrahydro-2H[1]benzothiopyrano[2,3-c]pyridine, 2-methyl-5-(4-dimethylamino phenyl)-1,3,4,10a-tetrahydro-2H[1]benzothiopyrano[2,3-c]pyridine and their non-toxic, pharmaceutically acceptable acid addition salts.

The novel process of the invention for the preparation of a compound of formula I comprises dehydrating a compound of the formula

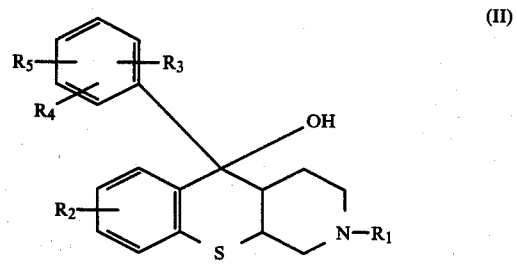

wherein $R_1$, $R_2$, $R_3$, $R_4$ and $R_5$ are as hereinbefore defined whereby the corresponding compound of formula I is obtained. The dehydration may, for example, be effected by means of a strong acid such as hydrochloric acid or sulfuric acid or of a base such as potassium bisulfate or by heating in hexametapol. The dehydration is preferably effected at reflux of the reaction mixture.

The compounds of formula II may, for example, be obtained, if desired, in situ by reaction of an organometallic compound of the formula

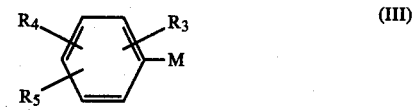

wherein $R_3$, $R_4$ and $R_5$ are as hereinbefore defined and M is lithium or a radical of formula MgHal wherein Hal is chlorine or bromine, any amino or alkylamino groups being optionally in protected form, with a compound of the formula

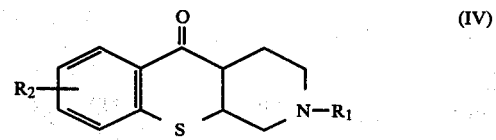

wherein $R_1$ and $R_2$ are as hereinbefore defined. The reaction is preferably effected in the presence of an anhydrous ether such as diethyl ether or tetrahydrofuran.

The compounds of formula III wherein M is lithium may conveniently be obtained, preferably in situ, by reaction of a compound of the formula

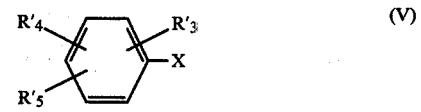

wherein X is a substituent selectively displaceable by lithium; $R_3'$, $R_4'$ and $R_5'$ are individually selected from the group consisting of hydrogen, halogen, alkyl of 1 to 5 carbon atoms, alkoxy of 1 to 3 carbon atoms, amino and alkylamino of 1 to 3 alkyl carbon atoms in protected form, or dialkylamino of 1 to 3 alkyl carbon atoms with an alkyl lithium such as n-butyl lithium. When $R_3'$, $R_4'$ and $R_5'$ represents a protected amino or alkylamino, the protecting group may, for example, be a trihydrocarbylsilyl wherein the hydrocarbyl groups may be the same or different e.g. a trialkylsilyl group such as bis(trimethylsilyl)amino. Such protecting groups may be removed, preferably by hydrolysis, either before reaction with the compound of formula IV or, if preferred, after reaction with the compound of formula IV.

The selectively displaceable substituent may, for example, be a halogen atom such as chlorine, bromine or iodine. Where one or more of $R_3'$, $R_4'$ and $R_5'$ is halogen, X should be a substituent which is more readily displaced. Thus, when one or more of $R_3'$, $R_4'$ and $R_5'$ is chlorine, X may be bromine or iodine.

The compounds of formula I may be converted into their acid addition salts by reaction with an acid, preferably in substantially equimolar quantities.

The compounds of formula IV, when they are not known, may be prepared by a process analogous to that described in Swiss Pat. No. 543,530. They may also be prepared by the methods described in British Pat. No. 1,252,131 and No. 1,252,132.

The novel antidepressant and neuroleptic compositions of the invention are comprised of an antidepressantly and neuroleptically effective amount of at least one compound of formula I and their non-toxic, pharmaceutically acceptable acid addition salts and an inert pharmaceutical carrier. The compositions may be in the form of tablets, dragees, gelatin capsules, granules, ampoules, suppositories and injectable solutions or suspensions.

Examples of suitable excipients are talc, gum arabic, lactose, starch, magnesium stearate, cocoa butter, aqueous or non-aqueous vehicles, fatty substances of animal or vegetable origin, paraffinic derivatives, glycols, various wetting, dispersing or emulsifying agents and/or preservatives.

The compositions of the invention have antidepressant and neuroleptic activity and have the advantage of being devoid of side-effects of presently used drug therapies such as the sedative, muscle relaxant and anticholinergic side effects of tricyclic antidepressant agents and the extrapyramidal effects of neuroleptics. The compositions are useful in the treatment of psychic, behavioral and personality disorders.

The novel method of the invention for inducing antidepressant and neuroleptic activity in warm-blooded animals, including humans, comprises administering an antidepressantly and neuroleptically effective amount of at least one compound of formula I and their non-toxic, pharmaceutically acceptable acid addition salts. The compounds may be administered orally, rectally or parenterally and the effective daily dose will vary depending on the compound selected, the method of administration and the condition being treated. The usual oral daily dose is 0.04 to 40 mg/kg.

In the following examples there are described several preferred embodiments to illustrate the invention. However, it is to be understood that the invention is not intended to be limited to the specific embodiments.

EXAMPLE 1

2-methyl-5-phenyl-1,3,4,10a-tetrahydro-2H-[1]-benzothiopyrano[2,3-c]pyridine hydrochloride

STEP A: 4-methoxycarbonyl-1-methylpyridinium iodide 700 g of methyl isonicotinate and 1.4 kg of methyl iodide were admixed in 2.0 liters of methanol and the resultant solution was stirred and refluxed for 5 hours. After cooling, the mixture was filtered off and the product was washed with ether and dried to obtain 1.385 kg of 4-methoxycarbonyl-1-methylpyridinium iodide (97.2% yield).

STEP B: Methyl 1,2,3,6-tetrahydro-1-methylisonicotinate

A suspension of 1.385 kg of 4-methoxycarbonyl-1-methylpyridinium iodide in 25 liters of dry methanol was stirred and cooled to 5° C. and 700 g of sodium borohydride were added thereto in portions over 1 hour with the temperature held at 5°–10° C. When the addition was complete, the resultant solution was stirred at room temperature for another hour and was then concentrated to 5 to 7 liters. 25 liters of water were added thereto followed by addition of 2 kg of solid sodium carbonate. The solution thus obtained was extracted 3 times with 2.5 liters of chloroform and the organic phase was dried over $Na_2SO_4$ and was evaporated to dryness. The residual oil was distilled to obtain 583 g of methyl 1,2,3,6-tetrahydro-1-methylisonicotinate (67.1% yield) boiling at 78° C. at 1 mm Hg.

STEP C: Methyl 1-methyl-3-(phenylthio)-isonipecotinate

A solution of 583 g of methyl 1,2,3,6-tetrahydro-1-methylisonicotinate, 373.5 ml of benzenethiol and 72.8 ml of piperidine in 7.28 liters of methanol was heated to reflux under nitrogen for 6 hours and was then cooled and concentrated to 2 liters. 8 liters of water were added thereto and the resultant solution was extracted 3 times with 2.5 liters of ethyl acetate. The organic layer was separated, washed twice with 5 liters of 1 N sodium hydroxide solution, twice with 5 liters of water, dried over sodium sulfate and evaporated to obtain 813 g of methyl 1-methyl-3-(phenylthio)-isonipecotinate (84.2% yield) which was used without further purification.

STEP D: 1,2,3,4,4a,10a-hexahydro-2-methyl-5H-[1]benzothiopyrano[2,3-c]pyridin-5-one 3.43 kg of tetraphosphoric acid were stirred and heated to 120° C. under an atmosphere of dry nitrogen and the heat source was removed. 327 g of methyl 1-methyl-3-(phenylthio)-isonipecotinate were added portionwise thereto over 30 minutes and the temperature rose to 135° C. and was maintained at this temperature for 4 hours. The resultant solution was cooled to 100° C., poured into 30 liters of vigorously stirred ice-cold water and allowed to stand until all the acid had dissolved. 50 w/w sodium hydroxide solution was added slowly thereto with good cooling to keep the temperature below 20° C. until the pH was raised to 7.0. The aqueous solution thus obtained was then extracted 3 times with 5 liters of ethyl acetate and the organic layer was separated washed with water, dried over sodium sulfate and evaporated to dryness. The residue was distilled to obtain 117.3 g of 1,2,3,4,4a,10a-hexahydro-2-methyl-5H-[1]-benzothiopyrano[2,3-c]pyridin-5-one (40.8% yield) with a boiling point of 156°–162° C. at 0.2 mm Hg.

STEP E:
2-methyl-5-phenyl-1,3,4,4a,5,10a-hexahydro-2H-[1]-benzothiopyrano[2,3-c]pyridin-5-ol 40 g of 1,2,3,4,4a,10a-hexahydro-2-methyl-5H-[1]-benzothiopyrano[2,3-c]pyridin-5-one were dissolved in 2 liters of dry ether and the solution obtaining was cooled to 5° C. in an ice bath while 220 ml (2 moles) of phenyl lithium were added dropwise thereto over 30 minutes with the temperature held below 0° C. When the addition was complete, the ice bath was removed and the solution thus obtained was stirred at room temperature for 30 minutes. 3 liters of water were added dropwise thereto and the resultant suspension was stirred vigorously for 2 hours and then was filtered. The product was washed with water and ether and was dried to obtain 20.5 g of 2-methyl-5-phenyl-1,3,4,4a,5,-10a-hexahydro-2H[1]benzothiopyrano[2,3-c]pyridin-5-ol (37% yield) melting at 176°–181° C.

STEP F:
2-methyl-5-phenyl-1,3,4,10a-tetrahydro-2H-[1]-benzothiopyrano[2,3-c]pyridine hydrochloride 21.4 g of 2-methyl-5-phenyl-1,3,4,4a,5,10a-hexahydro-2H-[1]benzothiopyrano[2,3-c]pyridin-5-ol were added to a solution of 42.8 ml of concentrated hydrochloric acid in 85.6 ml of water and the mixture obtained was refluxed for 1 hour with good stirring. On cooling, a white solid crystallized out which was filtered off to give 19.3 g of 2-methyl-5-phenyl-1,3,4,10a-tetrahydro-2H-1[1]benzothiopyrano[2,3-c]pyridine hydrochloride (90% yield) melting at 234°–40° C.

EXAMPLES 2 to 24

Using the procedure of Example 1, the compounds of formula I reported in Table I were prepared and the analyzed data and melting points are reported in Table II.

TABLE I

| Example No. | $R_1$ | $R_2$ | $R_5$ | M. Pt. HCl |
|---|---|---|---|---|
| 2 | $CH_3$ | H | 4-chlorophenyl | 215–8 |
| 3 | $CH_3$ | H | 4-methylphenyl | resub (229–35) 243–5 |
| 4 | $CH_3$ | H | 4-methoxyphenyl | 218–220 |
| 5 | $CH_3$ | H | 3-chlorophenyl | 201–3 |
| 6 | $CH_3$ | H | 4-(dimethylamino)phenyl | 243–5 |
| 7 | $CH_3$ | H | 3-methylphenyl | 204–6 |
| 8 | $CH_3$ | H | 3,4-dichlorophenyl | 214–6 |
| 9 | $CH_3$ | H | 4-ethylphenyl | 230–2 |
| 10 | $CH_3$ | H | 2-methylphenyl | 246–8 |
| 11 | $CH_3$ | H | 4-n-propoxyphenyl | 197–9 |
| 12 | $C_2H_5$ | H | phenyl | 211–3 |
| 13 | $CH_3$ | 7-Cl | phenyl | 221–5 |
| 14 | $CH_3$ | H | 3,4-dimethylphenyl | 208–10 |
| 15 | $CH_3$ | H | 4-aminophenyl | 230–2 |
| 16 | $CH_3$ | 8-$CH_3$ | phenyl | 205–7 |
| 17 | H | H | phenyl | 259.7 Auto |
| 18 | $CH_3$ | 9-$CH_3$ | phenyl | 221.8 Auto |
| 19 | $CH_3$ | H | 2,4-dimethylphenyl | 206–9 |
| 20 | $CH_3$ | 9-Cl | phenyl | 213–5 |
| 21 | $CH_3$ | 8-Cl | phenyl | 199–201 |
| 22 | $CH_3$ | 7-Cl | phenyl | 206–7 |
| 23 | $CH_3$ | H | 2,6-dimethylphenyl | 231–3 |
| 24 | $CH_3$ | H | 2,4,6-trimethylphenyl | 237–40 |

TABLE II

| Example No. | % C | % H | % N | % Cl | % S | Mass[b] Spec | Formula[c] |
|---|---|---|---|---|---|---|---|
| 2 | 62.64 / 62.15 | 5.26 / 5.20 | 3.84 / 3.76 | 19.46 / 19.75 | 8.80 / 8.75 | 327 | $C_{19}H_{19}NSCl_2$ |
| 3 | 69.85 / 69.19 | 6.45 / 6.34 | 4.07 / 3.93 | 10.31 / 10.47 | 9.32 / 9.12 | 307 | $C_{20}H_{22}NSCl$ |
| 4 | 66.74 / 66.56 | 6.16 / 6.12 | 3.89 / 3.76 | 9.85 / 9.75 | 8.91 / 8.69 | 322 | $C_{20}H_{22}CNSCl$ |
| 5 | 62.64 / 61.90 | 5.26 / 5.20 | 3.84 / 3.78 | 19.46 / 19.62 | 8.80 / 8.68 | 327 | $C_{19}H_{19}NSCl_2$ |
| 6 | 67.63 / 66.96 | 6.76 / 6.78 | 7.51 / 7.41 | 9.51 / 9.60 | 8.60 / 8.48 | 336 | $C_{21}H_{25}N_2SCl$ |
| 7 | 69.85 / 69.48 | 6.45 / 6.46 | 4.07 / 3.97 | 10.31 / 10.40 | 9.32 / 9.32 | 307 | $C_{20}H_{22}NSCl$ |
| 8 | 57.23 / 57.01 | 4.55 / 4.49 | 3.51 / 3.47 | 26.67 / 26.80 | 8.04 / 7.95 | 361 | $C_{19}H_{18}NSCl_3$ |
| 9[a] | 70.47 / 68.99 | 6.76 / 6.59 | 3.91 / 3.78 | 9.90 / 11.51 | 8.96 / 8.82 | 321 | $C_{21}H_{24}NSCl$ |
| 10 | 69.85 / 69.86 | 6.45 / 6.37 | 4.07 / 4.07 | 10.31 / 10.75 | 9.32 / 9.43 | 307 | $C_{20}H_{22}NSCl$ |
| 11 | 68.11 / 68.07 | 6.76 / 6.72 | 3.61 / 3.58 | 8.26 / 8.24 | 9.14 / — | 351 | $C_{22}H_{23}NOSCl$ |
| 12 | 69.85 / 69.37 | 6.45 / 6.39 | 4.07 / 4.02 | 10.31 / — | 9.32 / — | 307 | $C_{20}H_{22}NSCl$ |
| 13 | 62.64 / 62.87 | 5.26 / 5.32 | 3.84 / 3.79 | 19.46 / 19.15 | 8.80 / — | 327 | $C_{19}H_{19}NSCl_2$ |
| 14 | 70.47 / 70.21 | 6.76 / 6.74 | 3.91 / 3.80 | 9.90 / 10.20 | 8.96 / — | 321 | $C_{21}H_{24}NSCl$ |
| 15 | 59.84 / 59.45 | 5.82 / 5.80 | 7.34 / 7.02 | 18.59 / — | 8.51 / 8.17 | 302 | $C_{19}H_{12}N_2SCl_2$ |
| 16 | 69.85 / 69.29 | 6.45 / 6.39 | 4.07 / 4.01 | 10.31 / 10.42 | 9.32 / 9.24 | 307 | $C_{20}H_{22}NSCl$ |
| 17 | 68.45 / 68.25 | 5.74 / 5.89 | 4.44 / 4.36 | 11.22 / 10.83 | 10.15 / 9.97 | 279 | $C_{18}H_{18}NClS$ |
| 18[a] | 69.85 / 68.26 | 6.45 / 6.37 | 4.07 / 3.97 | 10.31 / 10.07 | 9.32 / 9.10 | 307 | $C_{20}H_{22}NSCl$ |
| 19 | 70.47 / 70.47 | 6.76 / 6.76 | 3.91 / 3.90 | 9.90 / 9.94 | 8.96 / 8.96 | 321 | $C_{21}H_{24}NSCl$ |
| 20 | 62.64 / 62.05 | 5.26 / 5.21 | 3.84 / 3.80 | 19.46 / 19.42 | 8.80 / 8.82 | 327 | $C_{19}H_{19}NSCl$ |
| 21 | 62.64 / 61.60 | 5.26 / 5.26 | 3.84 / 3.75 | 19.46 / 19.55 | 8.80 / 8.64 | 327 | $C_{19}H_{19}NSCl$ |
| 22 | 69.85 / 68.36 | 6.45 / 6.59 | 4.07 / 3.90 | 10.31 / 10.10 | 9.32 / 9.21 | 307 | $C_{20}H_{22}NSCl$ |
| 23 | 70.47 / 70.07 | 6.76 / 6.66 | 3.91 / 3.85 | 9.90 / 9.69 | 8.96 / 8.96 | 321 | $C_{21}H_{24}NSCl$ |
| 24 | 71.04 / 70.59 | 7.05 / 7.06 | 3.76 / 3.90 | 9.53 / 9.89 | 8.62 / 8.44 | 335 | $C_{22}H_{26}NSCl$ |

[a] Calculated for 0.5 M. $H_2O$:
[b] free base:
[c] HCl salt.

EXAMPLE 25
5-(4-aminophenyl)-2-methyl-1,3,4,10a-tetrahydro-2H-[1]benzothiopyrano[2,3-c]pyridine hydrochloride

STEP A:
5-(4-aminophenyl)-2-methyl-1,3,4,4a,5,10a-hexahydro-2H[1]-benzothiopyrano[2,3-c]pyridin-5-ol A solution of 3 g of p-chloro-N,N-bis(trimethylsilyl)aniline [prepared as in J.C.S., (1966), page 1706] in 30 ml of dry ether was treated with 12 ml of 1.6 M of n-butyl lithium in hexane. One hour later, 1.5 g of 1,2,3,4,4a,10a-hexahydro-2-methyl-2H-[1]-benzothiopyrano[2,3-c]pyridin-5-one were added thereto and the resultant mixture was stirred at room temperature for 2 hours. Water was then added and 2 hours later, the organic layer was separated, dried and evaporated to dryness to obtain 1.4 g of a solid residue. The residue was purified by chromatography over silica gel and was eluted with 5% methanol in chloroform to obtain 1 g of 5-(4-aminophenyl)-2-methyl-1,3,4,4a5,10a-hexahydro-2H-[1]benzothiopyrano-[2,3-c]pyridin-5-ol melting at 169° C.

STEP B:
5-(4-aminophenyl)-2-methyl-1,3,4,10a-tetrahydro-2H-[1]-benzothiopyrano[2,3-c]pyridine hydrochloride 1 g of the product of Step A was heated in refluxing 5.5 N hydrochloric acid for 2 hours and the resultant solution was then made basic by addition of sodium bicarbonate and was extracted with chloroform. The residue from the extract was dissolved in ethyl acetate and treated with a solution of hydrogen chloride in ethyl acetate to precipitate 0.8 g of 5-(4-aminophenyl)-2-methyl-1,3,4,10a-tetrahydro-2H-[1]benzothiopyrano[2,3-c]pyridine hydrochloride melting at 230°–2° C.

EXAMPLE 26

Tablets were prepared containing 25 mg of 2-methyl-5-(2,4-dimethylphenyl)-1,3,4,10a-tetrahydro-2H-[1]benzothiopyrano[2,3-c]pyridine hydrochloride and sufficient excipient of lactose, talc, starch, magnesium stearate for a final weight of 150 mg.

PHARMACOLOGICAL ACTIVITY

A. [$^3$H] Spiroperidol binding to neuroleptic receptors in membranes prepared from the striatum and frontal cortex of rats The binding of [$^3$H] spiroperidol to frontal cortex membranes appears to entail a major serotonergic component, whereas in striatal membranes the binding is predominantly dopaminergic [Leysen et al, Nature Vol. 272 (1978) p. 168–171] The ability of drugs to displace this radioligand from the frontal cortical receptors matches their activity in other models of serotonergic function, both for agonists and antagonists. Likewise, in striatal membranes, such activities predict the antidopaminergic action of neuroleptic drugs.

[Phenyl-4(n)-$^3$H] spiroperidol (Radiochemical Centre, TRK 570 21 Ci/mmol was used as the labelled ligand supplied as a 250 μCi/250 μl solution in ethanol and this solution was diluted 3.2/10,000 in assay buffer and 0.1 ml of this was added to 2 ml of binding assay.
=0.19 nM [$^3$H] spiroperidol
=0.08 μCi/binding assay The assay buffer was a modified 50 mM Tris HCl buffer with a pH of 7.6 and containing 120 mM of sodium chloride, 5 mM of potassium chloride, 1 mM of magnesium chloride, 2 mM of calcium chloride, 10 μM of pargyline and 0.1% of ascorbic acid.

The membrane preparation involved dissecting the frontal cortices or striata from 4 male CFHB rats according to J. Glowinski et al [Eur. J. Pharmacol., Vol. 49, (1978), P. 201–202]. The frontal cortex was taken as that cortical tissue in 'C', dorsal to a horizontal reference line passing through the point where the olfactory bulbs join the frontal cortex. The animals were killed by cervical dislocation and the dissected tissue was homogenized in 20 volumes of ice cold 0.32 M sucrose with a Teflon/glass homogeniser. The homogenate was centrifuged at 1000 g for 10 minutes and the resulting supernatant was recentrifuged at 30,000 g for 30 minutes. The supernatant was discarded and the pellet was resuspended by homogenization in 30 volumes of ice cold assay buffer.

Non-specific binding was accounted for by the inclusion of 1 μM (+) butaclamol in blank binding assays and this required a stock solution of 20 μM in distilled water. Solutions of displacing compounds were prepared at 20x final assay concentration in distilled water.

Binding assay protocol

Binding assays of 1.3 ml assay buffer, 0.5 ml membrane suspension, 0.1 ml distilled H$_2$O or drug solutions and 0.1 ml [$^3$H] spiroperidol dilution were made up in ice with the [$^3$H] spiroperidol being added last and incubated at 37° C. for 10 minutes. The bound ligand was separated by filtration through Whatman GF/C filters under vacuum followed by 2×10 ml rinses of ice cold assay buffer. The filters were dried at 80° C. and counted in 5 ml volumes of ECONOFLUOR (NEN). All binding assays, controls, blanks and each displacer concentration were run in triplicate. The [$^3$H] spiroperidol receptor binding displacement results on frontal cortex membranes (test A) and on striatal membranes (test B) are given in Table III below and the results are expressed as IC$_{50}$ (nM).

B. α-noradrenergic receptor binding in rat cortex membranes using [$^3$H] WB-4101

α-noradrenergic receptor sites in mammalian brain tissue can be labelled by the binding of [$^3$H] WB-4101 (2-[2',6'-dimethoxy]-phenoxymethylamino)-methylbenzodioxan), a potent α-adrenergic antagonist [Peroutka et al. Neuropharm. Vol. 16, p. 549–556 (1977)]. The potencies of neuroleptics and thymoleptics in competing for [$^3$H] WB-4101 binding sites correlate closely with their potencies in antagonising noradrenaline and adrenaline induced lethality in rats, confirming that affinity for [$^3$H] WB-4101 binding sites predicts α-receptor antagonism in vivo. The relative affinities of drugs for [$^3$H] WB-4101 binding sites provides an index of their relative propensities for eliciting autonomic side effects such as hypotension and sedation.

[$^3$H] WB-4101, Radiochemical Centre TRK 579, 20 Ci/mmol was used as a labelled ligand at a dilution of 1/10,000 in assay buffer. 0.1 ml of this solution was added to 2 ml (total) volume binding assay solutions.
=0.25 nM [$^3$H] WB-4101
=0.01 μCi/binding assay; p An adult male CFHB rat was killed by cervical dislocation and the brain was removed and placed in ice-cold 0.32 sucrose solution. The pons-medulla and cerebellum were removed and the forebrain was homogenized in 20 volumes of ice-cold 0.32 M sucrose using a Teflon/glass homogenizer. The homogenate was centrifuged at 1000 g for 10 minutes, the resulting pellet was discarded and the supernatant was recentrifuged at 30,000 g for 30 minutes. The supernatant was discarded and the pellet was resuspended by homogenization in 50 volumes of 50 mM pH 7.5 Tris HCl buffer (assay buffer).

Non-specific binding was accounted for by the inclusion of 100 μM noradrenaline in blank binding assays and this required a stock solution of 2 mM noradrenaline made up fresh every day in 0.1% ascorbic acid.

Solutions of displacing compounds were prepared 20X final assay concentration in assay buffer.

Binding assays of 1.3 ml assay buffer, 0.5 ml membrane suspension, 0.1 ml assay buffer or displacer solution and 0.1 ml [$^3$H] WB-4101 dilution were made up in ice with [$^3$H] ligand being added last, and incubated at 25° C. for 15 minutes. The bound ligand was separated by filtration through Whatman GF/C glass fibre filters under vacuum followed by 2×10 ml rinses of cold buffer. The filters were dried at 80° C. and counted in 5 ml volumes of ECONOFLUOR (NEN). All binding assays, controls, blanks and each displacer concentration were run in triplicate. The [$^3$H] WB-4101 receptor binding displacement results for rat cortical membranes (test C) are given in Table III and the results are expressed as IC$_{50}$ (nM).

C. Muscarinic chloinergic receptor binding in rat fore-brain membranes using [$^3$H] QNB Binding sites with high affinity and specificity for [$^3$H] QNB (quinuclidinyl benzilate) are present in homogenates of rat brain and the characteristics of the binding sites resemble those of muscarinic cholinergic receptors. Muscarinic antagonists and agonists displace specific [$^3$H] QNB binding in proportion to their pharmacological potency and the relative anticholinergic activities of anti-depressant and neuroleptic drugs have implications for their use in patients who might be adversely affected by anticholinergic effects [Snyder et al., Arch. Gen. Psychiat. Vol. 34 (2) (1977); p. 326-329] as a labelled ligand.

(3-[$^3$H]) Quinuclidinyl benzilate, Amersham TRK 506 16.4 Ci/mmol was used as a labelled ligand at a dilution of 1/10,000 in assay buffer and 0.1 ml of this solution was added to 2 ml of (total) volume binding assay solutions.

= 0.3 nM [$^3$H] QNB
= 0.1 µCi/binding assay

An adult male CFHB rat was killed by cervical dislocation and the brain was removed and placed in ice-cold 0.32 M sucrose solution. The pons-medulla and the cerebellum were removed and the forebrain was homogenized in 20 volumes of ice-cold 0.32 M sucrose using a Teflon/glass homogenizer. The homogenate was centrifuged at 1000 g for 10 minutes, the resulting pellet was discarded and the supernatant was recentrifuged at 30,000 g for 30 minutes. The supernatant was discarded and the pellet was resuspended by homogenization in 50 volumes of 50 mM pH 7.5 Tris HCl buffer. Non-specific binding was accounted for by the inclusion of 100 µM oxotremorine in blank binding assays and this required a stock solution of 2 mM oxotremorine in assay buffer (Tris HCl as above). Solutions of displacing compounds were prepared at 20X final assay concentration in assay buffer.

Binding assay protocol

Binding assay of 1.3 ml assay buffer, 0.5 ml membrane suspension, 0.1 ml assay buffer or drug solution and 0.1 ml [$^3$H] QNB dilution were made up in ice with the [$^3$H] QNB being added last, and incubated at 25° C. for 1 hour. The bound ligand was separated by filtration through Whatman GF/C glass fiber filters under vacuum followed by 2×10 ml rinses of cold buffer. The filters were dried at 80° C. and counted in 5 ml volumes of ECONOFLUOR (NEN). All binding assays, controls, blanks and each displacer concentration were run in triplicate. The [$^3$H] QNB receptor binding displacement results for rat forebrain membranes (test D) are given in Table III and the results are expressed as IC$_{50}$ values (nM).

D. Reversal of apomorphine hypothermia in mice

Whereas the reversal of the hypothermia induced in mice by low doses of apomorphine is a characteristic of classical neuroleptic agents, the hypothermia induced by high doses of this agent is specifically reversed by antidepressant drugs [Puech et al., In 'Advances in Pharmacology and Therapeutics Vol., 5' ed. Dumont, c. Pergamon p. 171-176 (1979)]. Groups of 10 male CD/1 mice (16-22 g) were dosed with vehicle or test drug intraperitoneally 30 minutes prior to the subcutaneously injection of apomorphine hydrochloride at 16 mg/kg. The rectal temperatures were recorded 30 minutes later using a rectal thermometer with digital readout. The ED$_{50}$ values (mg/kg) for the reversal of the hypothermia induced by apomorphine HCl in mice are shown in Table III (test E).

TABLE III

| Compound of Example | IC$_{50}$ (nM) | | | | |
|---|---|---|---|---|---|
| | test A | test B | test C | test D | test E |
| 1 | 250 | 1230 | 394 | 14,000 | 30 |
| 2 | 602 | 2600 | 692 | >100,000 | >40 |
| 3 | 25 | 154 | 29 | 73,600 | 20 |
| 4 | 131 | 955 | 120 | 62,000 | 15 |
| 5 | 427 | 3630 | 1950 | 16,200 | >40 |
| 6 | 112 | 309 | 100 | >100,000 | — |
| 7 | 251 | 2140 | 813 | 8,710 | >40 |
| 8 | 537 | 3310 | 631 | >100,000 | — |
| 9 | 50 | 490 | 59 | >100,000 | >40 |
| 10 | 105 | 1230 | 813 | 8,130 | 80 |
| 11 | 1250 | 9330 | 6760 | >100,000 | 22 |
| 12 | 398 | 3500 | 502 | 19,030 | — |
| 13 | 1480 | 6300 | 355 | 47,900 | >40 |
| 14 | 155 | 1469 | 502 | >100,000 | 30 |
| 15 | 158 | 1300 | 372 | 7,940 | 5 |
| 16 | 708 | 6310 | 1450 | 29,500 | — |
| 17 | 624 | 6760 | 676 | 19,500 | 35 |
| 18 | 174 | 1000 | 794 | 38,900 | >40 |
| 19 | 32 | 209 | 23 | 42,700 | — |
| 20 | 304 | 751 | 1050 | 67,750 | — |
| 21 | 1140 | 7010 | 3020 | 58,900 | >100 |
| 22 | 2450 | 9775 | 12500 | >100,000 | >100 |
| 23 | 331 | 4520 | 617 | 4,370 | >40 |
| 24 | 308 | 4330 | 617 | 1,180 | >40 |

From tests A and B, it can be seen that the tested compounds possess an important affinity for neuroleptic receptors but these compounds do not give rise to extrapyramidal effects typical of classical neuroleptic drugs. The results of test C indicate that some of these compounds possess little propensity for causing sedative and autonomic side effects, while test D indicates the low anti-cholinergic activities of the tested compounds. The results of test E show the anti-depressant activities of the tested compounds.

Various modifications of the compounds and processes of the invention may be made without departing from the spirit or scope thereof and it is to be understood that the invention is intended to be limited only as defined in the appended claims.

We claim:

1. A compound selected from the group consisting of compounds of the formula

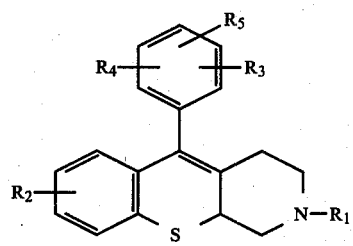

wherein R$_1$ is selected from the group consisting of hydrogen and alkyl of 1 to 5 carbon atoms, R$_2$ is selected from the group consisting of hydrogen, halogen and methyl, $R_3$, $R_4$ and $R_5$ are individually selected from the group consisting of hydrogen, halogen, alkyl of 1 to 5 carbon atoms, alkoxy of 1 to 3 carbon atoms, —NH$_2$ and mono- and dialkylamino of 1 to 3 alkyl carbon atoms and their non-toxic, pharmaceutically acceptable acid addition salts.

2. A compound of claim 1 wherein $R_1$ is methyl.

3. A compound of claim 2 wherein $R_2$ is hydrogen.

4. A compound of claim 1 selected from the group consisting of 2-methyl-5-phenyl-1,3,4,10a-tetrahydro-2H[1] benzothiopyrano[2,3-c]pyridine and its non-toxic, pharmaceutically acceptable acid addition salts.

5. A compound of claim 1 selected from the group consisting of 2-methyl-5-(4-tolyl)-1,3,4,10a-tetrahydro-2H[1] benzothiopyrano[2,3-c]pyridine and its non-toxic, pharmaceutically acceptable acid addition salts.

6. A compound of claim 1 selected from the group consisting of 2-methyl-5-(2,4-dimethylphenyl)-1,3,4,10a-tetrahydro-2H[1]benzothiopyrano[2,3-c]pyridine and its non-toxic, pharmaceutically acceptable acid addition salts.

7. A compound of claim 1 selected from the group consisting of 2-methyl-5-(4-dimethylaminophenyl)-1,3,4,10a-tetrahydro-2H[1]benzothiopyrano[2,3-c]pyridine and its non-toxic, pharmaceutically acceptable acid addition salts.

8. An antidepressant and neuroleptic composition comprising an antidepressantly and neuroleptically effective amount of at least one compound of claim 1 and a pharmaceutical carrier.

9. A composition of claim 8 wherein $R_1$ is methyl.

10. A composition of claim 8, wherein $R_2$ is hydrogen.

11. A composition of claim 8 wherein the compound is selected from the group consisting of 2-methyl-5-phenyl-1,3,4,10a-tetrahydro-2H[1]benzothiopyrano[2,3-c]pyridine and its non-toxic, pharmaceutically acceptable acid addition salts.

12. A composition of claim 8 wherein the compound is selected from the group consisting of 2-methyl-5-(4-tolyl)-1,3,4,10a-tetrahydro-2H[1]benzothiopyrano[2,3-c]pyridine and its non-toxic, pharmaceutically acceptable acid addition salts.

13. A composition of claim 8 wherein the compound is selected from the group consisting of 2-methyl-5-(2,4-dimethylphenyl)-1,3,4,10a-tetrahydro2H[1]benzothiopyrano[2,3-c]pyridine and its non-toxic, pharmaceutically acceptable acid addition salts.

14. A composition of claim 8 wherein the compound is selected from the group consisting of 2-methyl-5-(4-dimethylaminophenyl)-1,3,4,10a-tetrahydro-2H[1]benzothiopyrano[2,3-c]pyridine and its non-toxic, pharmaceutically acceptable acid addition salts.

15. The method of inducing antidepressant and neuroleptic acitivity in warm-blooded animals comprising administering to warm-blooded animals an antidepressantly and neuroleptically effective amount of at least one compound of claim 1.

16. The method of claim 15 wherein $R_1$ is methyl.

17. The method of claim 16 wherein $R_2$ is hydrogen.

18. A method of claim 15 wherein the compound is selected from the group consisting of 2-methyl-5-phenyl-1,3,4,10a-tetrahydro-2H-[1]benzothiopyrano[2,3-c]pyridine and its non-toxic, pharmaceutically acceptable acid addition salts.

19. A method of claim 15 wherein the compound is selected from the group consisting of 2-methyl-5-(4-tolyl) 1,3,4,10a-tetrahydro-2H[1]benzothiopyrano[2,3-c]pyridine and its non-toxic, pharmaceutically acceptable acid addition salts.

20. A method of claim 15 wherein the compound is selected from the group consisting of 2-methyl-5-(2,4-dimethylphenyl)-1,3,4,10a-tetrahydro-2H[1]benzothiopyrano[2,3-c]pyridine and its non-toxic, pharmaceutically acceptable acid addition salts.

21. A method of claim 15 wherein the compound is selected from the group consisting of 2-methyl-5(4-dimethylaminophenyl)-1,3,4,10a-tetrahydro-2H[1]benzothiopyrano[2,3-c]pyridine and its non-toxic, pharmaceutically acceptable acid addition salts.

* * * * *